United States Patent
Olesen et al.

(10) Patent No.: US 11,073,612 B2
(45) Date of Patent: Jul. 27, 2021

(54) FLOW ACCELERATION ESTIMATION DIRECTLY FROM BEAMFORMED ULTRASOUND DATA

(71) Applicant: B-K Medical Aps, Herlev (DK)

(72) Inventors: Jacob Bjerring Olesen, Copenhagen S. (DK); Carlos Armando Villagomez-Hoyos, Frederiksberg (DK); Jorgen Arendt Jensen, Horsholm (DK)

(73) Assignee: BK MEDICAL, APS, Herlev (DK)

( * ) Notice: Subject to any disclaimer, the term of this patent is extended or adjusted under 35 U.S.C. 154(b) by 644 days.

(21) Appl. No.: 15/745,459

(22) PCT Filed: Jul. 23, 2015

(86) PCT No.: PCT/IB2015/055592
§ 371 (c)(1),
(2) Date: Jan. 17, 2018

(87) PCT Pub. No.: WO2017/013474
PCT Pub. Date: Jan. 26, 2017

(65) Prior Publication Data
US 2018/0356519 A1    Dec. 13, 2018

(51) Int. Cl.
*G01S 15/50* (2006.01)
*A61B 8/04* (2006.01)
(Continued)

(52) U.S. Cl.
CPC .............. *G01S 15/50* (2013.01); *A61B 8/04* (2013.01); *A61B 8/06* (2013.01); *A61B 8/0883* (2013.01);
(Continued)

(58) Field of Classification Search
CPC .. G01S 15/50; G01S 7/52036; G01S 7/52026; G01S 7/52028; G01S 15/8915;
(Continued)

(56) References Cited

U.S. PATENT DOCUMENTS

| 5,285,788 A | 2/1994 | Arenson et al. |
| 5,522,393 A * | 6/1996 | Phillips ............... A61B 8/06 600/455 |

(Continued)

FOREIGN PATENT DOCUMENTS

| EP | 1300690 A1 | 4/2003 |
| JP | 4030288 B2 | 1/2008 |
| WO | 20070136554 A1 | 11/2007 |

OTHER PUBLICATIONS

International Search Report for PCT/IB2015/055592 published as WO2017/013474 dated Jan. 26, 2017.
(Continued)

*Primary Examiner* — Sanjay Cattungal
(74) *Attorney, Agent, or Firm* — Anthony M. Del Zoppo, III; Daugherty & Del Zoppo, Co. LPA

(57) ABSTRACT

A method for determining a flow acceleration directly from beamformed ultrasound data includes extracting a sub-set of data from the beamformed ultrasound data, wherein the sub-set of data corresponds to predetermined times and predetermined positions of interest, determining the flow acceleration directly from the extracted sub-set of data, and generating a signal indicative of the determined flow acceleration. An apparatus includes a beamformer (112) configured to processes electrical signals indicative of received echoes produced in response to an interaction of a transmitted ultrasound signal with tissue and generate RF data, and an acceleration flow processor (114) configured to directly process the RF data and generate a flow acceleration therefrom.

21 Claims, 3 Drawing Sheets

(51) Int. Cl.
*A61B 8/06* (2006.01)
*A61B 8/08* (2006.01)
*G01S 15/89* (2006.01)
*G01S 7/52* (2006.01)

(52) U.S. Cl.
CPC ........ *A61B 8/5207* (2013.01); *G01S 7/52026* (2013.01); *G01S 7/52028* (2013.01); *G01S 7/52036* (2013.01); *G01S 15/8915* (2013.01); *G01S 15/8997* (2013.01); *A61B 8/0891* (2013.01); *G01S 15/8984* (2013.01)

(58) Field of Classification Search
CPC ... G01S 15/8997; G01S 15/8984; A61B 8/04; A61B 8/06; A61B 8/0883; A61B 8/5207; A61B 8/0891
See application file for complete search history.

(56) References Cited

U.S. PATENT DOCUMENTS

| | | | |
|---|---|---|---|
| 6,725,076 | B1 | 4/2004 | Jensen |
| 8,211,024 | B2 | 7/2012 | Houle et al. |
| 2003/0125624 | A1* | 7/2003 | Shiki .................. G01S 15/8984 600/443 |
| 2005/0041837 | A1* | 2/2005 | Fan ........................ G06T 13/80 382/103 |
| 2007/0016037 | A1* | 1/2007 | Houle ..................... A61B 8/06 600/438 |
| 2008/0004904 | A1* | 1/2008 | Tran ..................... A61B 5/0022 705/2 |
| 2010/0185085 | A1 | 7/2010 | Hamilton |

OTHER PUBLICATIONS

Jensen, A. J. et al., Directional synthetic aperture flow imaging, IEEE Trans on US, Ferroelectrics and Frequency Control, vol. 51, No. 9, Sep. 1, 2004.

Noble, M., Left Ventricular Ejection in Conscious Dogs: I Measurement and Significance of the Maximum Acceleration of Blood from the Left Ventricle; Circ. Res. 1966;19:139-147; downloaded from http://circres.ahajournals.org/ Jul. 9, 2015.

Sabbah, H., Noninvasive evaluation of left ventricular performance based on peak aortic blood acceleration measured with a continuous-wave Doppler velocity meter; Diagnostic Methods, Ventricular Performance, Cir. 47, No. 2, 323-329, downloaded from http://circ.ahajournals.org/ Aug. 1986.

Dalsgaard, M.D, M., Isovolumic Acceleration Measured by Tissue Doppler Echocardiography Is PreLoad Independent in Healthy Subjects, Echocardiography: A Jrnl. of CV US and Allied Tech., vol. 24, No. 6,, 572-579; 2007.

Bastos, C., Spectrum of Doppler US SIgnals from Nonstationary Blood Flow, IEEE Trans. on US Ferroelectrics and Frequency Control, vol. 46, No. 5, Sep. 1999.

Sugawara, Ph.D., M., Noninvasive Estimation of Left Ventricular Max (dP/dt) from Aortic Flow Acceleration and Pulse Wave Velocity, Echocardiography: A Jrnl. of CV US and Allied Tech., vol. 11, No. 4, 377-384; 1994.

Ohtsuki, S. and Tanaka, M., Doppler Pressure Field Deduced from the Doppler Velocity Field in an Observation Plane in a Fluid, US in Med & Biol. vol. 29, No. 10, pp. 1431-1438, 2003.

Holen, J. et al., Determination of Pressure Gradient in Mitral Stenosis with a Non-invasive US Doppler Technique, Acta med. scand., vol. 199, pp. 455-460, 1976.

Hatle, L. et al., Noninvasive assessment of pressure drop in mitral stenosis by Doppler ultrasound, British Heart Journal, 1978, 40, 131-140; downloaded from http://heart.bmj.com/ Jul. 9, 2015.

Olesen, J. et al., Noninvasive Estimation of 2-D Pressure Gradients in Steady Flow Using Ultrasound, IEEE Trans. on US Ferroelectrics and Frequency Control, vol. 61, No. 8, Aug. 2014.

Savistzky, A. Smoothing and Differentiation of Data by Simplified Least Squares Procedures, Analytical Chemistry, vol. 36, No. 8, pp. 1627-1638, Jul. 1964.

Villagomez Hoyos, C. et al., Adaptive Multi-Lag for Synthetic Aperture Vector Flow Imaging, paper presented at the IEEE International US Symposium, Chicago, IL, 2014.

* cited by examiner

US 11,073,612 B2

FLOW ACCELERATION ESTIMATION DIRECTLY FROM BEAMFORMED ULTRASOUND DATA

RELATED APPLICATION

This application is a national filing of PCT application Serial No. PCT/IB2015/055592, filed Jul. 23, 2015, published as WO2017/013474 on Jan. 26, 2017. This application claims priority to PCT application Serial No. PCT/IB2015/055592, published as WO2017/013474 on Jan. 26, 2017.

TECHNICAL FIELD

The following generally relates to ultrasound imaging and more particularly to estimating temporal and/or spatial acceleration directly from beamformed ultrasound data.

BACKGROUND

An ultrasound imager can provide real-time structural images (e.g., a B-mode) of the interior of an object or a subject such as tissue, organs, etc. An ultrasound imager can also provide real-time images of flow (e.g., velocity) inside of a cavity such as the flow of blood cells in vascular tissue. In one instance, the flow image is super-imposed over the B-mode image, which provides a structural frame of reference for the flow image.

Flow acceleration has been used for clinical evaluation, including analyzing ventricular performance, studying hemodynamics, estimating pressure gradients in the circulatory system, etc. For example, Olesen et al., "Noninvasive estimation of 2-D pressure gradients in steady flow using ultrasound," IEEE Trans. Ultrason., Ferroelec., Freq. Contr., vol. 61, no. 8, pp. 1409-1418, 2014, discusses an approach to estimate pressure gradients from flow acceleration.

Flow acceleration estimation is especially used when deriving pressure through for instance the Navier-Stokes Equations. Spatial and temporal accelerations are calculated by differentiating velocity estimates. However, this approach is highly sensitive to the precision of the velocity estimates (and/or the velocity estimator estimating the velocity estimates), and the velocity estimates tend to be noisy.

Unfortunately, this leads to even higher noise levels of the derived acceleration as noise in the velocity field transfers directly to the acceleration estimate. The differential quotient increases the noise-level as the mathematical operator basically performs a high pass filtering of the velocity estimates, which primarily is governed by estimator noise. With these approaches, filtering (e.g., by means of Savitzky-Golay filters) and/or using a model and least squares analysis has been used to cope with the level of noise.

In view of at least the above, there is an unresolved need for another approach for estimating flow acceleration.

SUMMARY

Aspects of the application address the above matters, and others.

In one aspect, a method for determining a flow acceleration directly from beamformed ultrasound data includes extracting a sub-set of data from the beamformed ultrasound data, wherein the sub-set of data corresponds to predetermined times and predetermined positions of interest, determining the flow acceleration directly from the extracted sub-set of data, and generating a signal indicative of the determined flow acceleration.

In another aspect, an apparatus includes a beamformer configured to processes electrical signals indicative of received echoes produced in response to an interaction of a transmitted ultrasound signal with tissue and generate RF data, and an acceleration flow processor configured to directly process the RF data and generate a flow acceleration therefrom.

In another aspect a non-transitory computer readable storage medium is encoded with computer executable instructions which when executed by a processor of the computer causes the processor to: beamform ultrasound data acquired with an ultrasound imaging system producing RF ultrasound data, determine a double cross-correlation between a first sub-set of data from the RF ultrasound data and a second different sub-set of data from the RF ultrasound data, and determine a flow acceleration directly from the double cross-correlation.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings, in which like references indicate similar elements and in which.

DETAILED DESCRIPTION

The following generally describes a non-invasive approach for estimating flow acceleration (temporal and/or spatial) directly from ultrasound imaging measurements, i.e., independent of velocity estimates.

Figure 1:
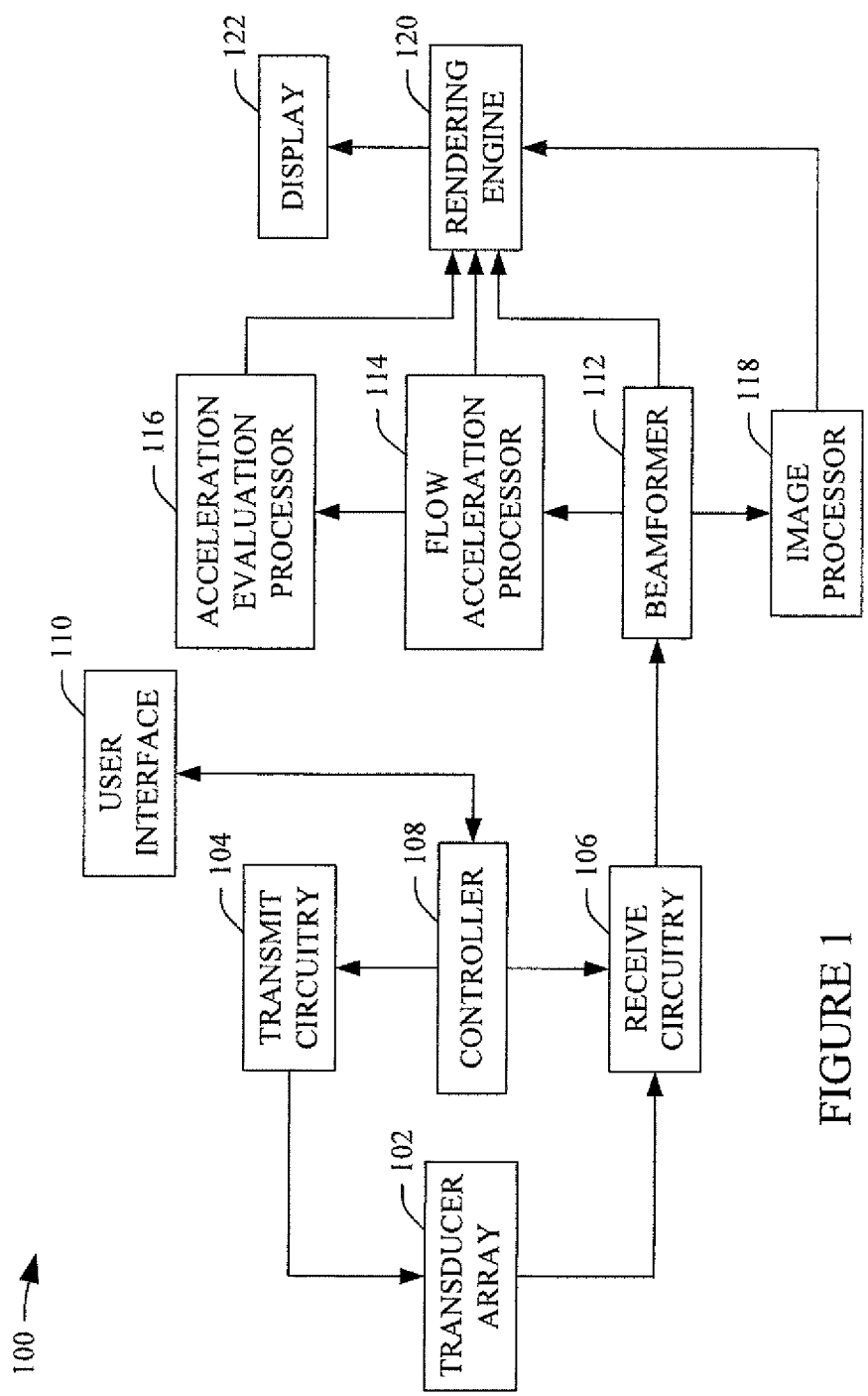
FIG. 1 schematically illustrates an example ultrasound imaging system with a flow acceleration processor.

Initially referring to FIG. 1, an example ultrasound imaging system 100 is illustrated.

A transducer array 102 includes one or more transducer elements, which are configured to transmit ultrasound signals and receive echo signals. Examples of suitable arrays include arrays with 1, 8, 16, 32, 64, 96, 128, 512, etc. transducer elements. The array 102 can be linear, curved, and/or otherwise shaped, fully populated or sparse and/or a combination thereof.

Transmit circuitry 104 generates a set of pulses that are conveyed to the transducer array 102. The set of pulses actuates a corresponding set of the transducer elements of the transducer array 102, causing the elements to transmit ultrasound signals into an examination or scan field of view.

Receive circuitry 106 receives echoes generated in response to the transmitted ultrasound signals from the transducer 102 and producing an electrical signal indicative thereof. The echoes, generally, are a result of the interaction between the emitted ultrasound signals and the structure (e.g., flowing blood cells, organ cells, etc.) in the scan field of view.

A controller 108 controls the transmit circuitry 104 and/or receive circuitry 106.

A user interface (UI) 110, which includes an input device (e.g., a button, a slider, a touch surface, etc.) and/or an output device (e.g., a visual and/or audible, etc.), provides an interface between the system 100 and a user of the system 100.

A beamformer 112 processes the electrical signal and generates beamformed or RF data at least for estimating a flow acceleration. In one instance, the beamformer 112 generates a sequence of focused, coherent echo samples along focused scanlines of a scanplane. In general, the beamformer 112 can generate 1-D, 2-D, 3-D, synthetic aperture, etc. and/or other ultrasound data. The beamformer 112 may also be configured to process the scanlines to lower speckle and/or improve specular reflector delineation via spatial compounding and/or perform other processing such as FIR filtering, IIR filtering, etc.

A flow acceleration processor 114 processes the RF data and determines. As described in greater detail below, the flow acceleration processor 114 is configured to process the RF data and estimate a flow acceleration (temporal and/or spatial) directly from the RF data, independent of velocity estimates. In one instance, this approach mitigates transferring noise from velocity estimates into the flow acceleration estimate relative to a configuration which derives the flow acceleration estimate from velocity estimates. In another instance, this approach could use another configuration which is not linked to the one used for the velocity estimates. Therefore, the acceleration range of estimates could be selected independently of the velocities and estimated more accurately. The resulting data is a more robust acceleration estimate and may mitigate a need for invasive catheters, thereby creating a safer and more problem-free work environment for the physician performing the estimate.

An acceleration evaluation processor 116 processes the flow acceleration estimate. This includes processing the flow acceleration estimate to analyze ventricular performance, study hemodynamics, estimate pressure gradients, etc. An example of computing intravascular pressure changes from temporal and spatial flow acceleration estimates is described in PCT/IB2015/054246, filed Jun. 4, 2015, and entitled "Non-invasive Estimation of Intravascular Pressure Changes using Vector Velocity Ultrasound (US)," the entirety of which is incorporated herein by reference.

An image processor 118 processes the beamformed data and generates one or more ultrasound images.

A rendering engine 120 visually presents an ultrasound image, the flow acceleration estimate, and/or information derived from the flow acceleration estimate.

A display 122 is configured to display the ultrasound image, the flow acceleration estimate (e.g., via numerical and/or graphical data).

In a variation, the ultrasound imaging system 100 further includes a velocity estimator configured to computer velocity and/or vector velocity information from the beamformed data. In this instance, the flow acceleration processor 114 can additionally be configured to estimate acceleration from the velocity and/or vector velocity information.

It is to be appreciated that the beamformer 112, the flow acceleration processor 114, the acceleration evaluation processor 116, and/or one or more other components of the system 100 can be implemented via a processor (e.g., a microprocessor, central processing unit, a controller, etc.) executing one or more computer readable instructions encoded or embedded on a non-transitory computer readable storage medium such as physical memory. The processor can additionally or alternatively execute a computer readable instruction carried by a carrier wave, a signal, or other transitory medium.

Figure 2:
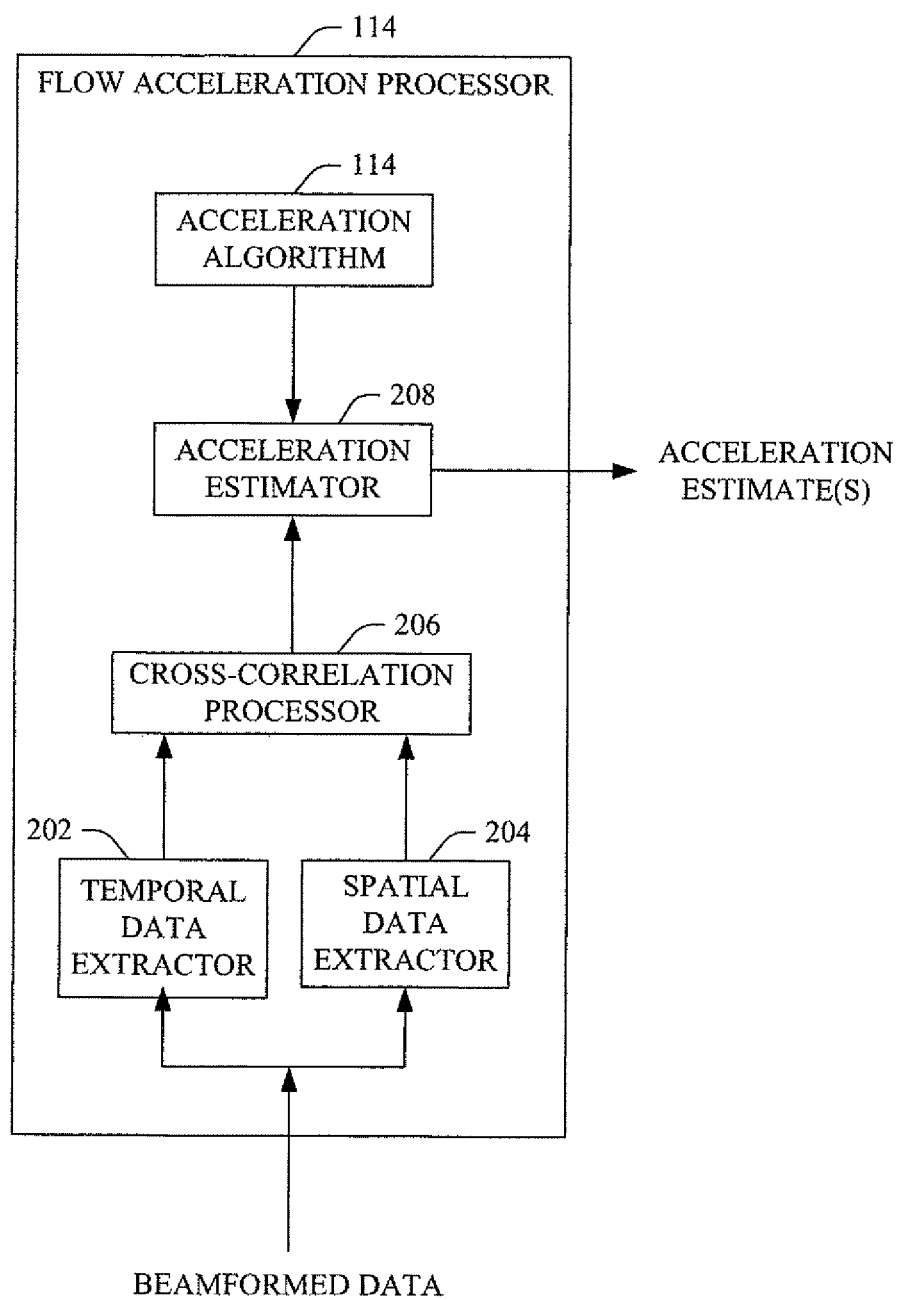
FIG. 2 schematically illustrates an example of the flow acceleration processor.

FIG. 2 illustrates an example of the flow acceleration processor 114.

The illustrated flow acceleration processor 114 includes a temporal data extractor 202. The temporal data extractor 202 extracts data based on time for computing a temporal acceleration. For example, the temporal data extractor 202 can extract data for different times and a same position.

The illustrated flow acceleration processor 114 further includes a spatial data extractor 204. The spatial data extractor 204 extracts data based on position for computing a spatial acceleration. For example, the spatial data extractor 204 can extract data for different positions and a same time.

In a variation, the spatial data extractor 204 is omitted. In another variation, the temporal data extractor 202 is omitted.

A cross-correlation processor 206 computes a cross-correlation between the data extracted at different times and at the same position and/or the data extracted at different positions and the same time. An example of a suitable cross-correlation approach is a double cross-correlation approach, such as the one described in Equation 1:

$$R_x(\tau) = \frac{1}{2L}\sum_{l=-L}^{L} R^{(1)}(l) R^{(1+K)}(l-\tau) \qquad \text{Equation 1}$$

where $R_x(\tau)$ is the double cross-correlation, $R^{(1)}$ and $R^{(1+K)}$ are cross-correlation functions, L is a length of the correlation function, l is an index, K is the indication of temporal or spatial distance between the correlation functions, and $\tau$ is the lag. In general, 2 L is the length of the segment of the cross-correlation functions. Examples of suitable lengths include, but are not limited to, two (2) to five (5) wavelengths, or less or more, as data is available for all time and all space.

The cross-correlation functions $R^{(1)}$ and $R^{(1+K)}$ can be computed as described in U.S. Pat. No. 6,725,076 B1, filed May 10, 2000, and entitled "Vector velocity estimation using directional beam forming and cross-correlation," and EP 1 300 690 A1, filed Oct. 2, 2001, and entitled "Apparatus and method for velocity estimation in synthetic aperture imaging," the entirety of which is incorporated herein by reference, and Jensen, "Directional Synthetic Aperture Flow imaging," IEEE Trans. Ultrason., Ferroelec., Freq. Contr., Vol. 51, NO. 9, September 2004. Other approaches are also contemplated herein.

In one instance, $R^{(1)}$ and $R^{(1+K)}$ are adjacent cross-correlation functions. For example, $R^{(1)}$ and $R^{(1+K)}$ can be the first and second (or next) time instances. However, $R^{(1)}$ and $R^{(1+K)}$ do not have to be adjacent cross-correlation functions. For example, $R^{(1)}$ and $R^{(1+K)}$ can be the first and third time instance, the first and fourth time instance, etc. This may be well-suited for an instance where there is low acceleration such that there is small shift between adjacent signals. In general, $R^{(1)}$ and $R^{(1+K)}$ can be the Nth and Kth time instance, since data for all time and all space is available if a synthetic aperture or plane wave sequence is used. Examples of such approaches are described in Villagomez-Hoyos et al., "Adaptive multi-lag for synthetic aperture vector flow imaging," in Proc. IEEE Ultrason. Symp., 2014, pp. 1722-1725, and Udesen et al., "High Frame-Rate Blood Vector Velocity Imaging Using Plane Waves: Simulations and Preliminary Experiments" IEEE Transactions on Ultrasonics Ferroelectrics and Frequency Control, Vol. 55, No. 8, 2008, p. 1729-1743.

An acceleration estimator 208 is configured to generate a flow acceleration estimate based on the cross-correlation estimate. For this, the acceleration estimator 208 processes the cross-correlation value for the different times and same position for the temporal acceleration, and process the cross-correlation value for the different positions and same times for the spatial acceleration. In the illustrated embodiment, the acceleration estimator 208 is configured to generate a temporal flow acceleration estimate ($Acc_t$) with an acceleration algorithm 210 such as the one described in Equation 2:

$$Acc_t = \frac{\tau_{max} c f_{prf}^2}{2Kf_s} \qquad \text{Equation 2}$$

where c is the speed of sound, $f_{prf}$ is a pulse-repetition frequency, $K/f_{prf}$ is a temporal distance between the correlation functions $R^{(1)}$ and $R^{(1+K)}$, $f_s$ is a sampling frequency and $\tau_{max}$ is a lag value where $R_x(\tau)$ has its maximum value.

In the illustrated embodiment, the acceleration estimator 208 is configured to generate a spatial flow acceleration estimate ($Acc_s$) with an acceleration algorithm 210 such as the one described in Equation 3:

$$Acc_s = \frac{\tau_{max} c f_{prf}}{2K\Delta r f_s} \qquad \text{Equation 3}$$

where c is the speed of sound, $f_{prf}$ is a pulse-repetition frequency, $K\Delta r$ is a spatial distance between the two correlation functions $R^{(1)}$ and $R^{(1+K)}$, and $f_s$ is a sampling frequency and $\tau_{max}$ is a lag value where $R_x(\tau)$ has its maximum value.

An increased accuracy in the output of the flow acceleration processor 114 is obtained if a polynomial is fitted to the discrete cross-correlation function $R_x(\tau)$ around its maximum. An example of a fitted polynomial is found at Foster et al., "Flow velocity profile via time-domain correlation: Error analysis and computer simulation." IEEE Transactions on Ultrasonics Ferroelectrics and Frequency Control, Vol. 37, 1990, p. 164-175.

The output of the flow acceleration processor 114 is the temporal and/or spatial acceleration estimates.

Figure 3:
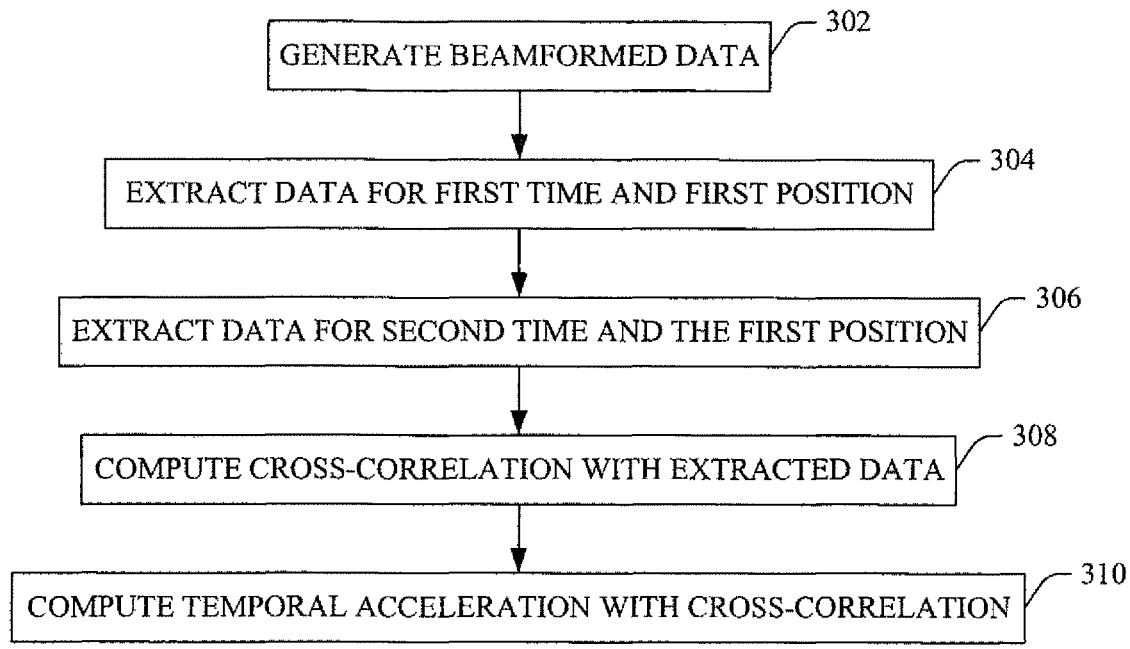
FIG. 3 illustrates an example method for determining a temporal acceleration directly from beamformed ultrasound data.

FIG. 3 illustrates an example method for determining a temporal acceleration directly from beamformed ultrasound data.

It is to be understood that the following acts are provided for explanatory purposes and are not limiting. As such, one or more of the acts may be omitted, one or more acts may be added, one or more acts may occur in a different order (including simultaneously with another act), etc.

At 302, electrical signals, generated in response to the transducer array 102 receiving and detecting echoes produced in response to an interaction of a transmitted ultrasound signal and tissue, are beamformed producing beamformed RF ultrasound data.

At 304, first ultrasound data for a first time and a first position is extracted from the beamformed ultrasound data.

At 306, second ultrasound data for a second time and the first position is extracted from the beamformed ultrasound data, where the first and second times are different times.

At 308, a double cross-correlation between the first and second ultrasound data is computed, as described herein (e.g., Equation 1) and/or otherwise, producing cross-correlation data.

At 310, an acceleration is estimated, as described herein (e.g., Equation 2) and/or otherwise, from the double cross-correlation data producing a temporal acceleration estimate.

The temporal acceleration estimate can be processed to derive information therefrom, which can be utilized for analyzing ventricular performance, studying hemodynamics, estimating pressure gradients in the circulatory system for diagnosing various cardiovascular diseases, etc.

Figure 4:
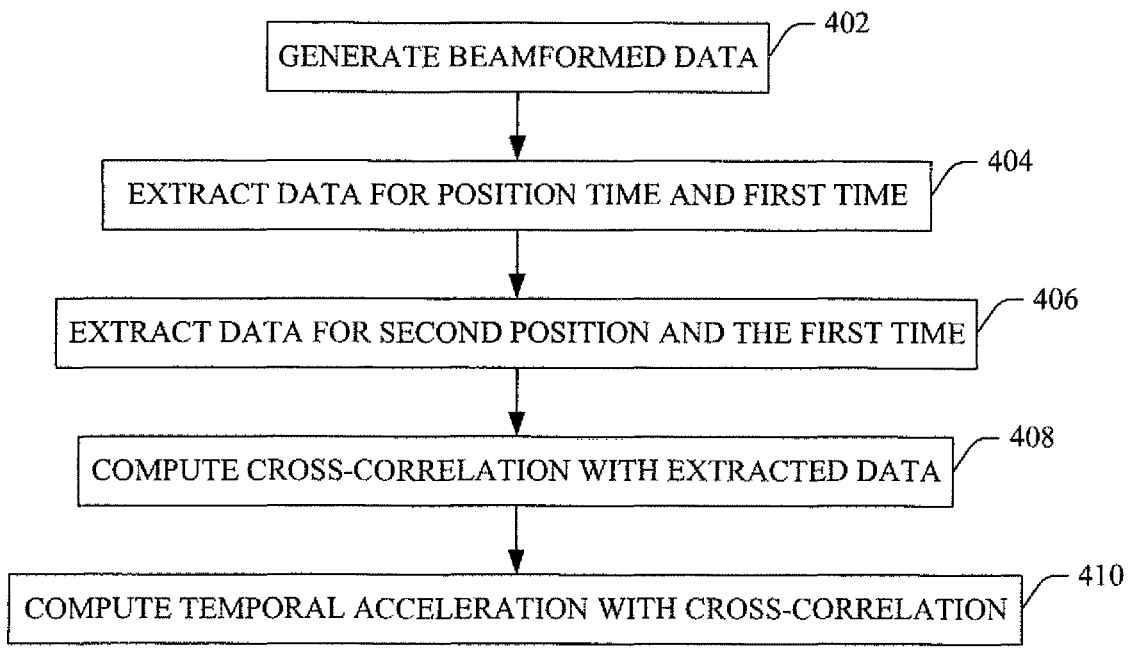
FIG. 4 illustrates an example method for determining a temporal acceleration directly from beamformed ultrasound data.

FIG. 4 illustrates an example method for determining a temporal acceleration directly from beamformed ultrasound data.

It is to be understood that the following acts are provided for explanatory purposes and are not limiting. As such, one or more of the acts may be omitted, one or more acts may be added, one or more acts may occur in a different order (including simultaneously with another act), etc.

At 402, electrical signals, generated in response to the transducer array 102 receiving and detecting echoes produced in response to an interaction of a transmitted ultrasound signal and tissue, are beamformed producing beamformed RF ultrasound data.

At 404, first ultrasound data for a first position and a first time is extracted from the beamformed ultrasound data.

At 406, second ultrasound data for a second position and the first time is extracted from the beamformed ultrasound data, where the first and second positions are different positions.

At 408, a double cross-correlation between the first and second ultrasound data is computed, as described herein (e.g., Equation 1) and/or otherwise, producing cross-correlation data.

At 410, an acceleration is estimated, as described herein (e.g., Equation 2 or 3) and/or otherwise, from the double cross-correlation data producing a spatial acceleration estimate.

The spatial acceleration estimate can be processed to derive information therefrom, which can be utilized for analyzing ventricular performance, studying hemodynamics, estimating pressure gradients in the circulatory system for diagnosing various cardiovascular diseases, etc.

Another method combines (in part, in full, and/or with additional and/or different acts) FIG. 3 and FIG. 4. In this instance, one or both of the temporal and spatial acceleration estimates can be processed to derive further information that can be utilized for analyzing ventricular performance, studying hemodynamics, estimating pressure gradients in the circulatory system for diagnosing various cardiovascular diseases, etc.

The methods described herein may be implemented via one or more processors executing one or more computer readable instructions encoded or embodied on computer readable storage medium such as physical memory which causes the one or more processors to carry out the various acts and/or other functions and/or acts. Additionally or alternatively, the one or more processors can execute instructions carried by transitory medium such as a signal or carrier wave.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A method for determining a flow acceleration directly from beamformed ultrasound data, the method comprising:

extracting a sub-set of data from the beamformed ultrasound data, wherein the sub-set of data corresponds to a predetermined time and a predetermined position of interest;

determining the flow acceleration directly from the extracted sub-set of data, including determining a temporal flow acceleration from extracted data from two different times and a same position and based on:

$$Acc_t = \frac{\tau_{max} c f_{prf}^2}{2Kf_s}$$

where Acc is the temporal flow acceleration, c is the speed of sound, $f_{prf}$ is a pulse-repetition frequency, $K/f_{prf}$ is a temporal distance between the correlation functions $R^{(1)}$ and $R^{(1+K)}$, $f_s$ is a sampling frequency and $\tau_{max}$ is a lag value where $R_x(\tau)$ has a maximum value; and generating a signal indicative of the determined flow acceleration.

2. The method of claim 1, further comprising:
generating an image with the beamformed ultrasound data;
generating indicia indicative of the determined flow acceleration; and
visually presenting the image with the indicia superimposed over the image.

3. The method of claim 1, further comprising:
deriving clinical information from the determined flow acceleration.

4. The method of claim 1, wherein determining the flow acceleration includes determining a spatial flow acceleration from extracted data from two different positions and a same time.

5. The method of claim 1, wherein determining the flow acceleration includes determining a double cross-correlation and determining the flow acceleration from the double cross-correlation.

6. The method of claim 5, wherein the double cross-correlation is determined based on:

$$R_x(\tau) = \frac{1}{2L} \sum_{l=-L}^{L} R^{(1)}(l) R^{(1+K)}(l-\tau)$$

where $R_x(\tau)$ is the double cross-correlation, $R^{(1)}$ and $R^{(1+K)}$ are cross-correlation functions, L is a length of the correlation function, K is an indication of temporal or spatial distance between the correlation functions, l is an index, and $\tau$ is a lag.

7. The method of claim 6, wherein $R^{(1)}$ and $R^{(1+K)}$ are adjacent cross-correlation functions.

8. The method of claim 6, wherein $R^{(1)}$ and $R^{(1+K)}$ are non-adjacent cross-correlation functions.

9. The method of claim 4, wherein the spatial flow acceleration is determined based on:

$$Acc_s = \frac{\tau_{max} c f_{prf}}{2K\Delta r f_s}$$

where c is the speed of sound, $f_{prf}$ is a pulse-repetition frequency, $K\Delta r$ is a spatial distance between the two correlation functions $R^{(1)}$ and $R^{(1+K)}$, and $f_s$ is a sampling frequency and $\tau_{max}$ is a lag value where $R_x(\tau)$ has a maximum value.

10. The method of claim 1, wherein the beamformed ultrasound data includes 1-D ultrasound data, and the determining of the flow acceleration includes determining of the flow acceleration directly from the 1-D ultrasound data.

11. The method of claim 1, wherein the beamformed ultrasound data includes 2-D ultrasound data, and the determining of the flow acceleration includes determining of the flow acceleration directly from the 2-D ultrasound data.

12. The method of claim 1, wherein the beamformed ultrasound data includes 3-D ultrasound data, and the determining of the flow acceleration includes determining of the flow acceleration directly from the 3-D ultrasound data.

13. The method of claim 1, wherein the beamformed ultrasound data includes synthetic aperture ultrasound data, and the determining of the flow acceleration includes determining of the flow acceleration directly from the synthetic aperture ultrasound data.

14. An apparatus, comprising:
a beamformer configured to processes electrical signals indicative of received echoes produced in response to an interaction of a transmitted ultrasound signal with tissue and generate RF data; and
an acceleration flow processor configured to directly process the RF data and generate a flow acceleration therefrom, wherein the acceleration flow processor determines a spatial flow acceleration based on:

$$Acc_t = \frac{\tau_{max} c f_{prf}^2}{2Kf_s}$$

where c is the speed of sound, $f_{prf}$ is a pulse-repetition frequency, $K\Delta r$ is a spatial distance between the two correlation functions $R^{(1)}$ and $R^{(1+K)}$ and $f_s$ is a sampling frequency and $\tau_{max}$, is a lag value where $R_x(\tau)$ has a maximum value.

15. The apparatus of claim 14, further comprising:
an image processor that generates an image with the RF data; and
a rendering engine that visually presents the image and the flow acceleration.

16. The apparatus of claim 14, further comprising:
an acceleration evaluation processor (116) that derives clinical information from the flow acceleration.

17. The apparatus of claim 14, wherein the acceleration flow processor determines a temporal flow acceleration from data of the RF data from two different times and a same position.

18. The apparatus of claim 14, wherein the acceleration flow processor determines the flow acceleration by determining a double cross-correlation and determining the flow acceleration from the double cross-correlation.

19. The apparatus of claim 18, wherein the double cross-correlation is determined based on:

$$R_x(\tau) = \frac{1}{2L}\sum_{l=-L}^{L} R^{(1)}(l)R^{(1+K)}(l-\tau)$$

where $R_x(\tau)$ is the double cross-correlation, $R^{(1)}$ and $R^{(1+K)}$ are cross-correlation functions, L is a length of the correlation function, K is an indication of temporal or spatial distance between the correlation functions, I is an index, and $\tau$ is a lag.

20. The apparatus of claim 17, wherein the acceleration flow processor determines temporal flow acceleration based on:

$$Acc_s = \frac{\tau_{max} c f_{prf}}{2K\Delta r f_s}$$

where Acc is the flow acceleration, c is the speed of sound, $f_{prf}$ is a pulse-repetition frequency, K is an intermediate step of correlation functions, is a sampling frequency and $\tau_{max}$ is a lag value where $R_x(\tau)$ has a maximum value.

21. A non-transitory computer readable storage medium encoded with computer executable instructions which when executed by a processor of the computer causes the processor to:
  beamform ultrasound data acquired with an ultrasound imaging system producing RF ultrasound data;
  determine a double cross-correlation between a first sub-set of data from the RF ultrasound data and a second different sub-set of data from the RF ultrasound data based on:

$$R_x(\tau) = \frac{1}{2L}\sum_{l=-L}^{L} R^{(1)}(l)R^{(1+K)}(l-\tau)$$

where $R_x(\tau)$ is the double cross-correlation, $R^{(1)}$ and $R^{(1+K)}$ are cross-correlation functions, L is a length of the correlation function, K is an indication of temporal or spatial distance between the correlation functions, I is an index, and $\tau$ is a lag; and
  determine a flow acceleration directly from the double cross-correlation.

* * * * *